US00PP30138P2

(12) United States Plant Patent
Ren

(10) Patent No.: US PP30,138 P2
(45) Date of Patent: Jan. 22, 2019

(54) ***ECHINACEA* PLANT NAMED 'BALSOMANITA'**

(50) Latin Name: *Echinacea x hybrida*
Varietal Denomination: Balsomanita

(71) Applicant: Ball Horticultural Company, West Chicago, IL (US)

(72) Inventor: Jianping Ren, Geneva, IL (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 15/732,062

(22) Filed: Sep. 11, 2017

(51) Int. Cl.
*A01H 5/02* (2018.01)

(52) U.S. Cl.
USPC ..... Plt./428

(58) Field of Classification Search
USPC ..... Plt./428
CPC . A01H 5/02; A01H 5/025; A01H 5/00; A01H 6/14
See application file for complete search history.

(56) References Cited

U.S. PATENT DOCUMENTS

PP28,162 P3 * 7/2017 Ren ..... Plt./428

OTHER PUBLICATIONS

Darwing Perennials *Echinacea* Sombrero Sangrita 2018, retrieved on Aug. 6, 2018, retrieved from the Internet at https://www.darwinperennials.com/Products/plantinfo/?phid=024102187037102, one page. (Year: 2018).*

Gulley Greenhouse 2017-2018 Pricing WeHoP Supplier, retrieved on Aug. 6, 2018, retrieved from the Internet at http://wehop.com/wp-content/uploads/Gulley-Greenhouse-2017-2018-Price-Level-1.pdf, pp. 11 and 28. (Year: 2017).*

* cited by examiner

*Primary Examiner* — June Hwu
(74) *Attorney, Agent, or Firm* — Audrey Charles

(57) ABSTRACT

A new and distinct cultivar of *Echinacea* plant named 'Balsomanita', characterized by its single-type, deep scarlet-red colored inflorescences, medium green-colored foliage, and moderately vigorous, compact-upright growth habit, is disclosed.

1 Drawing Sheet

Latin name of genus and species of plant claimed: *Echinacea* x *hybrida.*

Variety denomination: 'Balsomanita'.

BACKGROUND OF THE INVENTION

The present invention relates to a new and distinct cultivar of *Echinacea* plant botanically known as *Echinacea* x *hybrida* and hereinafter referred to by the cultivar name 'Balsomanita'.

The new cultivar originated in a controlled breeding program in Elburn, Ill. during August 2013. The objective of the breeding program was the development of *Echinacea* cultivars with a single inflorescence form having imbricate ray florets and a well-branched, compact growth habit.

The new *Echinacea* cultivar is the result of cross-pollination. The female (seed) parent of the new cultivar is the proprietary *Echinacea* x *hybrida* breeding selection coded E97A-1-1A-9-10, not patented, characterized by its single-type, dark red-purple colored ray florets, dark green-colored foliage, and moderately vigorous, semi-upright growth habit. The male (pollen) parent of the new cultivar is the proprietary *Echinacea* x *hybrida* breeding selection coded E100-2-2-10, not patented, characterized by its single-type, medium yellow-colored ray florets, medium green-colored foliage, and moderately vigorous, semi-upright growth habit. The new cultivar was discovered and selected as a single flowering plant within the progeny of the above stated cross-pollination during July 2014 in a controlled environment in Elburn, Ill.

Asexual reproduction of the new cultivar by in vitro shoot propagation since July 2014 in West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balsomanita' as a new and distinct cultivar of *Echinacea* plant:

1. Single-type, deep scarlet-red colored inflorescences;
2. Medium green-colored foliage; and
3. Moderately vigorous, compact-upright growth habit.

Plants of the new cultivar differ from plants of the female and male parents primarily in having a different ray floret color. In addition, the new cultivar has darker colored disc florets, receptacle spines and peduncles than the female or male parents.

Of the many commercially available *Echinacea* cultivars, the most similar in comparison to the new cultivar is SOMBRERO Baja Burgundy 'Balsombabur', U.S. Plant Pat. No. 28,162. However, in side by side comparisons, plants of the new cultivar differ from plants of 'Balsombabur' in at least the following characteristics:

1. Plants of the new cultivar larger diameter inflorescences than plants of 'Balsombabur';
2. Plants of the new cultivar have a ray floret color that is a lighter shade of red than plants of 'Balsombabur'; and
3. Plants of the new cultivar have darker red-coloration in the disc florets and receptacle spines than plants of 'Balsombabur'.

BRIEF DESCRIPTION OF THE PHOTOGRAPHS

The accompanying photographs show, as nearly true as it is reasonably possible to make the same in color illustrations of this type, typical inflorescence and foliage characteristics of the new cultivar. Colors in the photographs differ slightly from the color values cited in the detailed description, which accurately describes the colors of 'Balsomanita'. The plants were approximately 20-weeks old and grown in Elburn, Ill. in one-gallon containers for approximately 4 weeks in a greenhouse and 8 weeks outdoors.

DETAILED BOTANICAL DESCRIPTION

Figure 1:
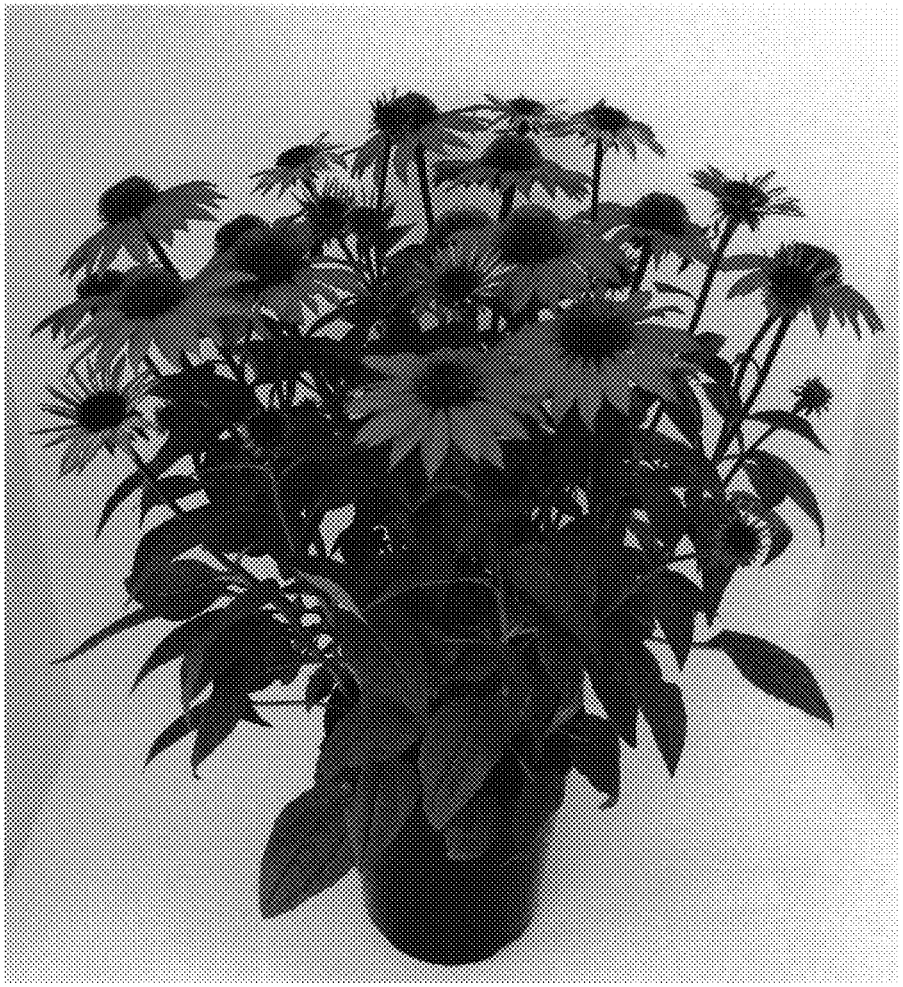
FIG. 1 illustrates a side view of the overall growth and flowering habit of 'Balsomanita'.
Figure 2:
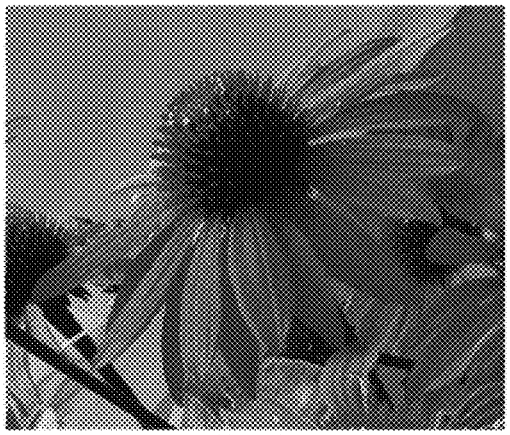
FIG. 2 illustrates a close-up view of an individual inflorescence of 'Balsomanita'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in July 2017 under natural light conditions in West Chicago, Ill.

The following descriptions and measurements describe approximately 20-week old plants produced from in vitro plantlets and grown utilizing a soilless growth medium under conditions comparable to those used in commercial practice. The plants were grown in Elburn, Ill. in one gallon containers in a glass-covered greenhouse for approximately 4 weeks and then outside for approximately 8 weeks. Greenhouse temperatures were maintained at approximately 60° F. to 65° F. (15.5° C. to 18.3° C.) during the day and approximately 55° F. to 60° F. (12.7° C. to 15.5° C.) during the night. No supplemental lighting was provided. Measurements and numerical values represent averages of typical plants.

Botanical classification: *Echinacea* x *hybrida* 'Balsomanita'.

Parentage:

*Female parent*.—Proprietary *Echinacea* x *hybrida* breeding selection coded E97A-1-1A-9-10, not patented.

*Male parent*.—Proprietary *Echinacea* x *hybrida* breeding selection coded E100-2-2-10, not patented.

Propagation:

*Type*.—In vitro propagation is preferred, divisions are possible.

*Time to initiate roots in vitro*.—Approximately 30 days at 18° C.

*Time to produce a rooted plantlet in summer*.—Approximately 30 days at 18° C.

*Root description*.—Fine, fibrous; grey to light brown in color.

*Rooting habit*.—Moderate density, moderate branching.

Plant description:

*Commercial crop time*.—Approximately 10 to 12 weeks from a rooted tissue culture plantlet to finish in a 15 cm container.

*Growth habit and general appearance*.—Herbaceous perennial, moderately vigorous, compact-upright.

*Hardiness*.—USDA Zone 5a (−20° F. to −15° F./−28.9° C. to −26° C.).

*Size*.—Height from soil level to top of plant plane: Approximately 44.0 cm. Width: Approximately 46.0 cm.

*Branching habit*.—No lateral branching, flowering stems grow from base. Quantity of main stems per plant: Approximately 7.

*Stems*.—Strength: Very strong. Aspect: Nearly erect. Shape: Rounded. Length to base of inflorescence: Approximately 28.0 cm. Diameter: Approximately 6.0 mm to 1.0 cm. Length of central internode: Approximately 5.0 cm. Texture: Densely pubescent with short strigose hairs. Color of young stems: 144A to 144B. Color of mature stems: 144A to 144B with an overlay of 187A.

Foliage description:

*General description*.—Form: Simple. Arrangement: Alternate.

*Leaves*.—Aspect: Perpendicular to stem, subtending with age. Shape: Narrowly ovate to lanceolate. Margin: Entire to shallowly serrate, slightly undulate. Apex: Acute. Base: Attenuate. Venation pattern: Pinnate. Length of mature leaf: Approximately 9.0 cm. Width of mature leaf: Approximately 4.5 cm. Texture of upper surface: Dull, moderately pubescent with short strigose hairs. Texture of lower surface: Moderately pubescent with short strigose hairs. Color of upper surface of young and mature foliage: Closest to 137A with venation of 147C, midvein occasionally has overlay of 187A. Color of lower surface of young and mature foliage: Closest to 147B with venation of 147D.

*Petiole*.—Shape: V-shaped. Length: Approximately 4.0 cm to 9.0 cm. Diameter: Approximately 3.0 mm. Texture of upper surface: Glabrous. Texture of lower surface: Sparsely covered with very short strigose hairs. Color of upper and lower surfaces: 147D occasionally with an overlay of 187A.

Flowering description:

*Flowering habit*.—'Balsomanita' is freely flowering under outdoor growing conditions blooming from spring through autumn and with limited flowering under short winter days in a greenhouse environment.

*Lastingness of individual inflorescence on the plant*.—Approximately 3 weeks.

Inflorescence description:

*General description*.—Type: Solitary, composite. Persistent. Shape: Conical. Aspect: Facing upward. Arrangement: Terminal, held upright on strong peduncles. Fragrance: Faintly sweet. Quantity per plant: Approximately 16. Height: Approximately 3.5 cm. Diameter: Approximately 9.5 cm.

*Peduncle*.—Strength: Strong. Aspect: Erect to approximately 45° from vertical. Length: Approximately 13.5 cm. Diameter: Approximately 4.0 mm to 5.0 mm. Texture: Densely pubescent with short strigose hairs. Color: 144A to 144B with a heavy overlay of 187A.

*Bud*.—Quantity per plant: Approximately 7. Shape: Flattened globular with immature ray florets nearly erect. Length: Approximately 1.5 cm. Diameter: Approximately 2.0 cm. Color: Outer ray florets of 154D with an overlay of 187C; bud center of 143A with 187A.

*Ray florets*.—Quantity per inflorescence: Approximately 22. Arrangement: In a single whorl, slightly imbricate. Aspect: Perpendicular to disc, subtending slightly with age, twisting absent. Shape: Elliptic to narrowly obovate. Appearance: Dull. Margin: Entire. Apex: Emarginate to notched. Base: Attenuate. Length: Approximately 4.5 cm. Width: Approximately 1.2 cm. Texture of upper surface: Glabrous, ribbed longitudinally. Texture of lower surface: Sparsely pubescent, ribbed longitudinally. Color of upper surface when first open: N25B with 44A to 44B. Color of lower surface when first open: 65C with a heavy overlay of 71A. Color of upper surface when fully open: 44B to 44A, with age darkening to 44A with 45A. Color of lower surface when fully open: 70D to 70B.

*Disc florets*.—Disc diameter: Approximately 4.0 cm. Quantity per inflorescence: Approximately 265. Arrangement: Spirally arranged in center of inflorescence. Shape: Tubular. Margin of free portion: Entire. Apex: Five acute tips. Base: Fused into a tube. Length: Approximately 1.0 cm. Diameter: Approximately 2.0 mm. Texture: Glabrous. Color of upper or inner surface when first and fully open: 145C with 187A at tips. Color of lower or outer surface when first and fully open: Upper third 187A, midsection of 145B and base of 155D.

*Receptacle*.—Shape: Conical. Height: Approximately 1.6 cm. Diameter: Approximately 1.5 cm. Color: 155D.

*Phyllaries*.—Quantity per inflorescence Approximately 60. Arrangement: In four whorls. Appearance: Dull, stiff. Shape: Narrowly ovate to lanceolate, strongly curved towards the peduncle. Margin: Entire, ciliate. Apex: Acute. Base: Truncate. Length: Approximately 1.0 cm. Width: Approximately 2.0 to 3.0 mm. Texture of upper or inner surface: Glabrous. Texture of lower or outer surface: Sparsely pubescent with short strigose hairs. Color of upper surface: 137A. Color of lower surface: 137B.

*Receptacle spines*.—Number of spines per disc: Approximately 265. Shape: Acicular. Length: Approximately 1.3 cm. Width at widest point: Approximately 2.0 mm. Apex: Acute. Base: Truncate. Texture: Glabrous. Color: Apex of 167B with a heavy overlay and tip of 187A, mid-section of 144A, and base of 155D.

*Reproductive organs*.—Androecium: Present on disc florets only. Stamen quantity: 5 per floret. Anther shape: Oblong, basifixed. Anther length: Approximately 3.0 mm. Anther color: Closest to 203B. Filament length: Approximately 2.0 mm. Filament color: 145D. Pollen amount: Moderate. Pollen color: 14A. Gynoecium: Present on disc florets only. Pistil quantity: 1 per floret. Pistil length: Approximately 1.0 cm. Stigma shape: Bifid. Stigma length: Approximately 2.0 mm. Stigma color: 187A. Style length: Approximately 6.0 mm. Style color: 145D. Ovary length: Approximately 3.0 mm. Ovary color: 155D.

Seed and fruit production: Neither seed nor fruit production has been observed.

Disease and pest resistance: No particular resistance or susceptibility to other diseases or insects noted to date.

What is claimed is:

1. A new and distinct cultivar of *Echinacea* plant named 'Balsomanita', substantially as herein illustrated and described.

* * * * *